United States Patent [19]

Gosselink et al.

[11] Patent Number: 5,371,308
[45] Date of Patent: Dec. 6, 1994

[54] PROCESS FOR THE PREPARATION OF LOWER OLEFINS

[75] Inventors: John W. Gosselink; Jacobus Eilers, both of Amsterdam, Netherlands

[73] Assignee: Shell Oil Company, Houston, Tex.

[21] Appl. No.: 111,797

[22] Filed: Aug. 25, 1993

[30] Foreign Application Priority Data

Aug. 25, 1992 [EP] European Pat. Off. ......... 92202601.8

[51] Int. Cl.$^5$ ............................................. C07C 4/04
[52] U.S. Cl. ..................................... 585/251; 585/324;
585/648; 585/930; 208/58; 208/89; 208/950
[58] Field of Search ............. 585/251, 324, 648, 650,
585/638, 930; 208/950, 89, 58

[56] References Cited

U.S. PATENT DOCUMENTS

| | | | |
|---|---|---|---|
| 3,130,007 | 4/1964 | Breck . | |
| 3,536,605 | 10/1970 | Kittrell . | |
| 3,932,552 | 1/1976 | Starks . | |
| 4,080,397 | 3/1978 | Deer et al. | 585/251 |
| 4,257,871 | 3/1981 | Wernicke et al. | 585/251 |
| 4,260,474 | 4/1981 | Wernicke et al. | 288/57 |
| 4,548,702 | 10/1985 | York et al. | 288/89 |
| 4,579,986 | 4/1986 | Sie . | |
| 4,900,429 | 2/1990 | Richardson | 208/418 |

FOREIGN PATENT DOCUMENTS

| | | |
|---|---|---|
| 084151A1 | 7/1983 | European Pat. Off. . |
| 0104672 | 4/1984 | European Pat. Off. . |
| 0110449 | 6/1984 | European Pat. Off. . |
| 0127220 | 12/1984 | European Pat. Off. . |
| 0127253 | 12/1984 | European Pat. Off. . |
| 0161705 | 11/1985 | European Pat. Off. . |
| 161705A2 | 11/1985 | European Pat. Off. . |
| 0167215 | 1/1986 | European Pat. Off. . |
| 0180269 | 5/1986 | European Pat. Off. . |
| 0221598 | 5/1987 | European Pat. Off. . |
| 0428223 | 5/1991 | European Pat. Off. . |
| 1305054 | 1/1973 | United Kingdom . |
| 1451617 | 10/1976 | United Kingdom . |
| 1461989 | 1/1977 | United Kingdom . |
| 1531640 | 11/1978 | United Kingdom . |
| 2014970 | 9/1979 | United Kingdom . |

*Primary Examiner*—Anthony McFarlane

[57] ABSTRACT

A process for preparing lower olefins from a hydrocarbon feed having at least a fraction boiling above the boiling point range of the lower olefins, which process includes thermal cracking of the hydrocarbon feed, wherein at least part of the hydrocarbon feed is a hydroprocessed synthetic oil fraction. The hydroprocessed synthetic oil fraction may be prepared by hydrogenation and/or hydroconversion and/or hydrocracking of a synthetic oil fraction.

15 Claims, No Drawings

PROCESS FOR THE PREPARATION OF LOWER OLEFINS

I. FIELD OF THE INVENTION

The present invention relates to a process for preparing lower olefins from a hydrocarbon feed having at least a fraction boiling above the boiling point range of the lower olefins. The process includes thermal cracking of the hydrocarbon feed.

II. BACKGROUND OF THE INVENTION

Lower olefins, that is, olefins having from 2 to 4 carbon atoms, are particularly suitable starting materials for use in a large number of chemical processes, such as, alkylation, oligomerization and polymerization processes. The preparation of lower olefins from a hydrocarbon feed by thermal cracking of that feed is a well known process and is commercially applied at a large number of petrochemical complexes. Typically, a distillate fraction of a crude oil, commonly a naphtha fraction of a crude oil, is used as a hydrocarbon feed in the thermal cracking process.

For commercial reasons, there is a demand for a thermal cracking process having a high selectivity towards lower olefins and avoiding as much as possible the formation of methane. To minimize the formation of methane, the thermal cracking process is carried out at conditions of relatively low severity. However, a fairly large proportion of the hydrocarbon feed remains uncracked. In contrast, if the thermal cracking process is carried out at relatively high severity conditions, thereby increasing the hydrocarbon conversion, a fairly large proportion of the hydrocarbon feed is cracked to methane. Accordingly, an optimum thermal cracking process would combine a high conversion of the hydrocarbon feed with a high selectivity to lower olefins.

It has been disclosed in European Patent Application No. 161705 (EP 161705) that a fraction of the product of a Fischer-Tropsch synthesis process may be used as a hydrocarbon feed in the thermal cracking process. EP 161705 relates to a process for the preparation of linear $C_{10}-C_{20}$ olefins, comprising converting, at elevated temperature and pressure and using a specific catalyst, a mixture of carbon monoxide and hydrogen into a mixture of hydrocarbons, substantially consisting of linear paraffins (Fischer-Tropsch product), and converting a heavy fraction of the mixture of hydrocarbons, substantially consisting of $C_{20-}+$ paraffins, into linear $C_{10}-C_{20}$ olefins by mild thermal cracking. The $C_{19}-$ fraction of the mixture of hydrocarbons, substantially consisting of linear paraffins, may be converted into lower olefins by thermal steam cracking. It was found that, when using this $C_{19}-$ fraction as a feed for a thermal cracking process, the selectivity towards lower olefins was increased, as compared with a naphtha fraction of a crude oil.

III. SUMMARY OF THE INVENTION

It has now been found that the selectivity of the thermal cracking process towards lower olefins can be further and significantly increased when use is made of a synthetic oil fraction, such as a Fischer-Tropsch product, as hydrocarbon feed in the thermal cracking process, which synthetic oil fraction has been hydroprocessed.

Accordingly, the present invention provides a process for preparing lower olefins from a hydrocarbon feed having at least a fraction boiling above the boiling point range of the lower olefins, which process comprises thermal cracking of the hydrocarbon feed, wherein at least part of the hydrocarbon feed is a hydroprocessed synthetic oil fraction.

IV. DESCRIPTION OF THE PREFERRED EMBODIMENTS

For the purpose of this specification, the term "hydroprocessed synthetic oil fraction" is used to indicate that the oil fraction is derived from a synthesis process, such as a Fischer-Tropsch process or an oligomerization process, and subsequently treated in a process in the presence of hydrogen.

The amount of the hydroprocessed synthetic oil fraction present in the hydrocarbon feed is not critical and may vary within wide limits. Typically, the hydrocarbon feed may further comprise a suitable distillate fraction of a crude oil or a synthetic oil fraction. The more hydroprocessed synthetic oil fraction present in the feed, the higher the selectivity of the thermal cracking process towards lower olefins. The hydroprocessed synthetic oil fraction may constitute up to 100% by weight of the hydrocarbon feed. However, it may be desired to use a hydrocarbon feed comprising, for example, 5% by weight of a hydroprocessed synthetic oil fraction, depending on the market prices of the lower olefins, the hydroprocessed synthetic oil fraction and the other components in the hydrocarbon feed. Preferably, the hydrocarbon feed comprises at least 20%, more preferably at least 50% by weight, of the hydroprocessed synthetic oil fraction. Even more preferably, the hydrocarbon feed comprises at least 90% by weight of the hydroprocessed synthetic oil fraction.

The boiling point range of the hydrocarbon feed may vary within wide limits. Typically, the hydrocarbon feed has a 96% by weight boiling point of at most 560° C. It will be understood that boiling points and boiling point ranges are those at atmospheric pressure. Preferably, the hydrocarbon feed has a boiling point range of from 30° C. to 350° C. More preferably, the hydrocarbon feed has a boiling point range of from 30° C. to 200° C. It is to be understood that the hydroprocessed synthetic oil fraction may constitute the higher boiling fraction or the lower boiling fraction of the hydrocarbon feed. Typically, the hydroprocessed synthetic oil fraction may have a boiling range lying in substantially the same range as the boiling range of the total hydrocarbon feed.

The severity of the thermal cracking process depends to some extent on the heaviness, that is the boiling point range, of the hydrocarbon feed. Thus, a hydrocarbon feed having a relatively low boiling point range, may require less severe thermal cracking conditions as compared to a hydrocarbon feed having a relatively high boiling point range. Accordingly, the thermal cracking conditions may vary within wide limits. Typically, the thermal cracking is carried out at a temperature of from 500° C. to 1200° C., preferably of from 700° C to 1000° C, more preferably of from 750° C. to 900° C. The thermal cracking is typically carried out at a pressure of from 0.1 to 15 bar abs., preferably of from 1 to 5 bar abs.

The residence time of the hydrocarbon feed in a thermal cracking unit, may vary, depending, for example, on the heaviness of the hydrocarbon feed and the thermal cracking conditions applied. Typically, the thermal cracking is carried out at a residence time of from 0.01 to 1.0 seconds, preferably of from 0.04 to 0.5 seconds.

The thermal cracking of the hydrocarbon feed is typically carried out in the presence of an inert gaseous diluent, preferably nitrogen or steam, more preferably steam. The amount of inert gaseous diluent to be applied, is not critical and may vary within wide limits but typically, the inert gaseous diluent is present in an amount of frown 20 to 100 parts by weight per 100 parts by weight of the hydrocarbon feed.

In one embodiment, the hydroprocessed synthetic oil fraction present in the hydrocarbon feed to the thermal cracking process, may be prepared by hydrogenation of a synthetic oil fraction, at elevated temperature and pressure in the presence of hydrogen and a hydrogenation catalyst. The action of the hydrogenation stage is, for example, to hydrogenate any unsaturated hydrocarbons and oxygenares present in the synthetic oil without substantial hydrocracking occurring. Preferably, the hydrogenation is carried out at a temperature of from 100° C. to 300° C., more preferably at a temperature of from 150° C. to 275° C., in particular of from 175° C. to 250° C. The hydrogenation may be carried out at a relatively wide range of pressures, but preferably, the hydrogenation is carried out at a hydrogen partial pressure of from 5 bar to 150 bar, more preferably of from 20 bar to 120 bar.

The hydrogenation may be carried out using any type of catalyst bed arrangement, such as a fluidized bed, moving bed, slurry phase bed or a fixed bed, each type of catalyst bed having its own characteristic advantages and disadvantages. However, preferably a fixed catalyst bed is applied. It is to be understood that the reaction conditions, such as temperature, pressure and space velocity, may vary according to the specific type of catalyst bed being used. If a fixed catalyst bed is being used, the synthetic oil feed is preferably provided at a weight hourly space velocity of from 0.1 kg/l/h to 5 kg/l/h, more preferably at a weight hourly space velocity of from 0.25 kg/l/h to 2.5 kg/l/h. Hydrogen may be applied to the hydrogenation stage at a gas hourly space velocity in the range of from 100 to 10000 Nl/l/hr, more preferably from 250 to 5000 Nl/l/hr. The ratio of hydrogen to the feed may range from 100 to 5000 Nl/kg and is preferably from 250 to 2500 Nl/kg.

Hydrogenation catalysts are well known in the art and are commercially available in a large variety of compositions. Typically, the hydrogenation catalyst comprises as catalytically active component one or more metals selected from Groups VIb and VIII of the Periodic Table of the Elements. In particular the metal is selected from the group consisting of molybdenum, tungsten, cobalt, nickel, ruthenium, iridium, osmium, platinum, palladium, and mixtures thereof. Preferably, the catalyst comprises one or more metals selected from nickel, platinum and palladium as the catalytically active component. A particularly suitable catalyst comprises nickel as a catalytically active component.

Hydrogenation catalysts typically comprise a refractory metal oxide or silicate as a carrier. Suitable carrier materials include silica, alumina, silica-alumina, zirconia, titania and mixtures thereof. Preferred carrier materials for inclusion in the hydrogenation catalyst are silica, alumina and silica-alumina.

The hydrogenation catalyst may comprise the catalytically active component in an amount of from 0.05 to 80 parts by weight, preferably from 0.1 to 70 parts by weight, calculated as metal(s) per 100 parts by weight of total catalyst. The amount of catalytically active metal present in the catalyst will vary according to the specific metal concerned. A particularly suitable hydrogenation catalyst comprises nickel in an amount in the range of from 30 to 70 parts by weight, calculated as metal per 100 parts by weight of total catalyst.

Suitable hydrogenation catalysts are available commercially, or may be prepared by methods well known in the art, for example, mulling, impregnation or precipitation.

In another embodiment of the present invention, the hydroprocessed synthetic oil fraction is prepared by hydroconversion of a synthetic oil fraction, at elevated temperature and pressure in the presence of hydrogen and a hydroconversion catalyst.

Generally, the synthetic oil fraction used as feed for the preparation of the hydroprocessed synthetic oil fraction by hydroconversion, will have a higher boiling point range as compared to the synthetic oil fraction used as feed for the preparation of the hydroprocessed synthetic oil fraction by hydrogenation.

The conditions at which the hydroconversion is carried out depend upon the boiling point range of the feed and the desired boiling point range of the product of the hydroconversion process. The major reactions occurring during the hydroconversion process are a hydrogenation of the feed, a hydroisomerization of the feed and a hydrocracking of the heavier components in the feed. The extent to which one reaction may prevail over the other reactions, is dependent upon the particular conditions being applied and the particular catalyst being used.

Typically, the hydroconversion is carried out at a temperature of from 175° C. to 400° C., preferably of from 250° C. to 375° C. Typical hydrogen partial pressures range from 10 to 250 bars and are preferably in the range of from 25 to 150 bars.

The hydroconversion may be carried out using any type of catalyst bed arrangement, such as a fluidized bed, moving bed, slurry phase bed or a fixed bed, each type of catalyst bed having its own characteristic advantages and disadvantages. However, a fixed catalyst bed is preferably applied. It is to be understood that the reaction conditions, such as temperature, pressure and space velocity, may vary according to the specific type of catalyst bed being used. If a fixed catalyst bed is being used, the synthetic oil feed is preferably provided at a weight hourly space velocity of from 0.1 kg/l/h to 5 kg/l/h, more preferably at a weight hourly space velocity of from 0.25 kg/l/h to 2 kg/l/h. Hydrogen may be supplied at a gas hourly space velocity of from 100 to 10000 Nl/l/hr, preferably from 500 to 5000 Nl/l/hr. The ratio of hydrogen to the feed may range from 100 to 5000 Nl/kg and is preferably from 250 to 2500 Nl/kg.

Typical hydroconversion catalysts comprise as catalytically active component one or more metals selected from Groups VIB and VIII of the Periodic Table of Elements. In particular the metal is selected from molybdenum, tungsten, cobalt, nickel, ruthenium, iridium, osmium, platinum, and palladium. Preferably, the hydroconversion catalyst comprises one or more metals selected from nickel, platinum and palladium as the catalytically active component. Hydroconversion catalysts comprising platinum as the catalytically active component have been found to be particularly suitable.

Hydroconversion catalysts typically comprise a refractory metal oxide or silicate as a carrier. The carrier material may be amorphous or crystalline. Suitable carrier materials include silica, alumina, silica-alumina, zirconia, titania and mixtures thereof. The carrier may comprise one or more zeolites, either alone or in combination with one or more of the aforementioned carrier materials. Preferred carrier materials for inclusion in the hydroconversion catalyst are silica, alumina and silica-alumina. A particularly preferred catalyst comprises platinum supported on a silica-alumina carrier.

The catalyst may comprise the catalytically active component in an amount of from 0.05 to 80 parts by weight, preferably from 0.1 to 70 parts by weight, calculated as metal(s) per 100 parts by weight of total catalyst. The amount of catalytically active metal present in the catalyst will vary according to the specific metal concerned. A particularly preferred hydroconversion catalyst comprises platinum in an amount in the range of from 0.05 to 2 parts by weight, more preferably from 0.1 to 1 parts by weight, calculated as metal per 100 parts by weight of total catalyst.

Suitable hydroconversion catalysts for use in preparation of the hydroprocessed synthetic oil fraction are available commercially, or may be prepared by methods well known in the art, for example, mulling, impregnation or precipitation.

In a further embodiment, the hydroprocessed synthetic oil fraction is prepared by hydrocracking of a synthetic oil fraction, at elevated temperature and pressure in the presence of hydrogen and a hydrocracking catalyst. General ly, the synthetic oil feed for the preparation of the hydroprocessed synthetic oil fraction by hydrocracking, will have a higher boiling point range as compared to the synthetic oil feed for the preparation of the hydroprocessed synthetic oil fraction by hydrogenation.

Typically, the hydrocracking is carried out at a temperature of from 250° C. to 500° C., preferably of from 300° C. to 450° C. Typical hydrogen partial pressures range from 10 to 300 bars and are preferably in the range of from 25 to 200 bars.

The hydrocracking may be carried out using any type of catalyst bed arrangement, such as a fluidized bed, moving bed, slurry phase bed or a fixed bed, each type of catalyst bed having its own characteristic advantages and disadvantages. However, preferably a fixed catalyst bed is applied. It is to be understood that the reaction conditions, such as temperature, pressure and space velocity, may vary according to the specific type of catalyst bed being used. If a fixed catalyst bed is being used, preferably, the synthetic oil feed is provided at a weight hourly space velocity of from 0.1 kg/l/h to 10 kg/l/h, more preferably at a weight hourly space velocity of from 0.2 kg/l/h to 5 kg/l/h. The ratio of hydrogen to the feed may range from 100 to 5000 Nl/kg and is preferably from 250 to 2000 Nl/kg.

Typically, the hydrocracking catalyst comprises a zeolitic carrier. Preferred carriers include zeolites of the faujasite type, in the presence of an inorganic oxide binder. Examples of zeolites of the faujasite type include synthetic zeolite Y as described in U.S. Pat. No. 3,130,007, ultrastable Y as described in U.S. Pat. No. 3,536,605, and ultrahydrophobic Y as described in British Patent Application No. 2,014,970. Typically, the carrier of the hydrocracking catalyst comprises 5–90% by weight of a faujasite type zeolite and 10–95% by weight of an amorphous or crystalline inorganic oxide binder. Examples of suitable binders comprise alumina, magnesia, titania, clays and mixtures thereof, optionally in the presence of other inorganic oxides such as, zirconia and silica. Alumina is a preferred binder.

Typically, the hydrocracking catalyst further comprises one or more metal component(s) of Group VIb and/or VIII of the Periodic Table of the Elements, preferably one or more components of nickel and/or cobalt and one or more components of molybdenum and/or tungsten. Preferably, the metal component(s) in the hydrocracking catalyst range from 0.05 to 10% by weight of Group VIII metal component(s) and from 2 to 40% by weight of Group VIb metal component(s), calculated as metal(s) per 100 parts by weight of total catalyst. The metal component(s) in the hydrocracking catalyst may be in the oxidic and/or sulfidic form, in particular in the sulfidic form. If a combination of at least a Group VIb and a Group VIII metal component is present as (mixed) oxides, it will normally be subjected to a sulfiding treatment prior to proper use in hydrocracking.

Suitable hydrocracking catalysts are available commercially, or may be prepared by methods well known in the art, for example, impregnation or precipitation of the metal component(s) on the carrier.

It will be understood that any combination of the above mentioned processes may be applied to prepare the hydroprocessed synthetic oil fraction. Accordingly, the hydroprocessed synthetic oil fraction may be prepared by hydrogenation and/or hydroconversion and/or hydrocracking of a synthetic oil fraction. In a preferred embodiment of the present invention, the hydroprocessed synthetic oil fraction is prepared by hydrogenation and hydroconversion and/or hydrocracking of a synthetic oil fraction. More preferably, the hydroprocessed synthetic oil fraction is prepared by hydrogenation, followed by hydroconversion and/or hydrocracking of a synthetic oil fraction.

Typically, the synthetic oil fraction, used to prepare the hydroprocessed synthetic oil fraction, is prepared by a Fischer-Tropsch synthesis process to prepare a synthetic oil, followed by (vacuum) distillation to obtain a desired synthetic oil fraction. Fischer-Tropsch synthesis is the name commonly given to processes in which hydrocarbons are prepared from a mixture of carbon monoxide and hydrogen by contacting the mixture at elevated temperature and pressure with a suitable catalyst. Catalysts for use in the Fischer-Tropsch synthesis process frequently comprise, as the catalytically active component, a metal from Group VIII of the Periodic Table of Elements. Particularly preferred catalytically active metals include ruthenium, iron, cobalt and nickel. Especially preferred synthetic oils are those prepared by a Fischer-Tropsch synthesis process employing a catalyst comprising cobalt as the catalytically active component.

The catalytically active metal is preferably supported on a porous carrier. The porous carrier may be selected from any of the suitable refractory metal oxides or silicates or combinations thereof known in the art. Particular examples of preferred porous carriers include silica, alumina, titania and mixtures thereof. Silica is a particularly preferred carrier material for the catalyst used in the preparation of the synthetic oils.

The amount of catalytically active metal on the carrier is preferably in the range of from 3 to 100 pbw per 100 pbw of carrier material, more preferably from 10 to 80 pbw, especially from 20 to 60 pbw.

If desired, the catalyst may also comprise one or more metals or metal oxides as promoters. Suitable metal oxide promoters may be selected from Groups IIA, IIIB, IVB, VB and VIB of the Periodic Table of Elements, or the actinides and lanthanides. In particular, oxides of magnesium, calcium, strontium, barium, scandium, yttrium. lanthanum, cerium, titanium, zirconium, hafnium, thorium, uranium, vanadium and chromium are most suitable promoters. A particularly preferred metal oxide promoter for the catalyst used to prepare the synthetic oil is zirconium oxide. Suitable metal promoters may be selected from Groups VIIB of VIII of the Periodic Table. Rhenium and Group VIII noble metals are particularly suitable, with platinum and palladium being especially preferred. The amount of promoter present in the catalyst is preferably in the range of from 0.1 to 150 pbw per 100 pbw of carrier.

A particularly suitable catalyst for use in preparing the synthetic oil is a cobalt/zirconium/silica catalyst. Examples of suitable catalysts which may be used are disclosed in European Patent Application Nos. EP 0 104 672, EP 0 110 449, EP 0 127 220, EP 0 167 215, EP 0 180 269 and EP 0 221 598.

As mentioned, the synthetic oil may be prepared by the Fischer-Tropsch synthesis, in which a mixture of carbon monoxide and hydrogen is contacted with a catalyst as hereinbefore described. The synthesis is typically conducted at a temperature of from about 125° C. to about 350° C., preferably from about 175° C. to 250° C. Typical operating pressures for the synthesis are in the range of from about 5 to 100 bar, more preferably from about 10 to 50 bar. During the synthesis process, the catalyst is typically contacted with a gaseous mixture comprising hydrogen and carbon monoxide in a ratio of less than 2.5, preferably less than 1.75. More preferably, the hydrogen to carbon monoxide ratio of the mixture is in the range of from 0.4 to 1.5, especially from 0.9 to 1.3.

Accordingly, in a preferred embodiment, the hydroprocessed synthetic oil fraction for use as a feed to the thermal cracking process according to the present invention, is prepared by preparation of a synthetic oil from a synthesis gas mixture by a Fischer-Tropsch process as described hereinbefore, followed by hydroprocessing in the way as described hereinbefore, and optionally intermediate (vacuum) distillation.

It may be desirable to operate the process according to the present invention in an energy-efficient way. Therefore it is desirable that the process according to the present invention is operated on the same location as the process for the preparation of the synthesis gas, the Fischer-Tropsch synthesis process and the process for the preparation of the hydroprocessed synthetic oil fraction. In this way optimal use can be made of any waste heat streams and/or any waste streams of steam or nitrogen. In a particularly preferred embodiment of the present invention, the heat produced upon cooling of a synthesis gas stream derived from a synthesis gas production unit, is used in the thermal cracking unit for carrying out the process of the present invention. Typically, the synthesis gas stream is cooled from about 1200° C. to about 500° C., prior to introduction in a Fischer-Tropsch synthesis process reactor, by heat exchange of the synthesis gas stream with the hydrocarbon feed to the thermal cracking unit. More preferably, the synthesis gas stream is first cooled from about 1200° C. to about 1000° C. to provide heat for driving the cracking reaction in the thermal cracking process of the present invention, and secondly cooled from about 1000° C. to about 500° C. to provide heat for vaporization and heating of the hydrocarbon feed to the thermal cracking process. In a further embodiment of the invention, any excess steam produced in, for example, a Fischer-Tropsch synthesis reactor may be used in the thermal steam cracking process according to the present invention. Hydrogen in tail gas from the thermal cracker may be used to adjust the $H_2/CO$ ratio of the synthesis gas to be used in the Fischer-Tropsch synthesis reactor, or in the hydroprocessing of a synthetic oil fraction to produce a hydroprocessed synthetic oil fraction.

V. ILLUSTRATED AND COMPARATIVE EXAMPLES

The invention will now be illustrated by means of the following Examples.

Experimental conditions of the thermal cracking process were varied in experiments using different feeds, so as to arrive at a comparable methane make.

EXAMPLE 1

Preparation of synthetic oil fraction

A synthesis gas mixture, having a $H_2/CO$ ratio of 1.1, was fed to a reactor containing a fixed bed of a catalyst comprising cobalt (18.3 %wt., calculated as cobalt oxide), zirconium (8.5 %wt., calculated as zirconium oxide) and silica. The catalyst was prepared by a process as described in European Patent Application No. 428 223. The reactor was operated under the following conditions:
Temperature 210°–225° C.
Pressure 36 bar
Space velocity 1125 Nl.1 $^{-1}.h^{-1}$
The $C_5+$ yield was 90 wt.

EXAMPLE 2

Preparation of hydroprocessed synthetic oil fraction

The $C_5-C_9$ fraction of the product of Example 1, was hydrogenated in a reactor containing a fixed bed of a nickel containing catalyst commercially available from Harshaw. The reactor was operated under the following conditions:
Temperature 220° C.
Hydrogen partial pressure 30 bar
Space velocity 1 kg.l$^{-1}$.h$^{-1}$
Hydrogen/feed ratio 1000 Nl/kg
The hydrogenation resulted in little cracking and the yield of hydrogenated $C_5+$ was 99.2 %wt.

EXAMPLE 3

Preparation of lower olefins

The $C_5+$ product of Example 2 was cracked in the presence of nitrogen, as inert diluent, at an average temperature of 840° C., an average pressure of 2.25 bar, a residence time of 0.2 seconds and a nitrogen/hydrocarbon feed ratio of 0.8. The $C_2-C_4$ olefins yield amounted to 71.3 %wt of which 47.0 %wt. ethene, 15.2 %wt. propene and 8.1 %wt. $C_4$-olefins. The methane make amounted to 13.7 %wt. The remaining 15.0 %wt. boiled in the $C_5+$ range.

EXAMPLE 4

Preparation of hydroprocessed synthetic oil fraction

The $C_{20}+$ fraction of the product of Example 1, was hydroconverted in a reactor containing a fixed bed of a catalyst comprising 0.8 parts by weight of platinum per 100 parts by weight of silica-alumina carrier. The catalyst was prepared by a process described in British Patent No. 1 451 617. The reactor was operated under the following conditions:
Temperature 335° C.
Hydrogen partial pressure 30 bar
Space velocity 1.33 kg.l$^{-1}$.h$^{-1}$ The hydroconverted product was distilled to obtain a C$_5$–C$_9$ fraction.

EXAMPLE 5

Preparation of lower olefins

The C$_5$–C$_9$ fraction of the product of Example 4 was cracked in the presence of nitrogen at an average temperature of 820° C., an average pressure of 2.25 bar, a residence time of 0.2 seconds and a nitrogen/hydrocarbon feed ratio of 0.8. The C$_2$–C$_4$ olefins yield amounted to 66.4%wt., of which 35%wt. ethene, 18.4%wt. propene and 12.1%wt. C$_4$-olefins. The methane make amounted to 13.3 wt. The remaining 20.3%wt. boiled in the C$_5$+ range.

COMPARATIVE EXAMPLE A

Preparation of lower olefins

A straight-run C$_5$–C$_9$ fraction of a Crude Oil, was cracked under the conditions of Example 5. The C$_2$–C$_4$ olefins yield amounted to only 56.7%wt., of which 27.6%wt. ethene, 17.2%wt. propene and 11.4%wt. C$_4$-olefins. The methane make amounted to 12.9%wt. The remaining 30.4%wt. boiled in the C$_5$+ range.

COMPARATIVE EXAMPLE B

Preparation of lower olefins

A C$_5$–C$_9$ fraction of the synthetic oil of Example 1, was cracked under the conditions of Example 3. The C$_2$–C$_4$ olefins yield amounted to only 63.2%wt., of which 40.1%wt. ethene, 13.9%wt. propene and 8.3%wt. C$_4$-olefins. The methane make amounted to 12.9%wt. The remaining 23.9%wt. boiled in the C$_5$+ range.

What is claimed is:

1. A process for preparing lower olefins from a hydrocarbon feed having at least a fraction boiling above the boiling point range of the lower olefins, which process comprises thermal cracking of the hydrocarbon feed wherein at least part of the hydrocarbon feed is a hydroprocessed synthetic oil fraction, prepared by a Fischer-Tropsch synthesis process, comprising contacting at elevated temperature and pressure a synthesis gas with a catalyst, comprising a metal selected from Group VII of the Periodic Table.

2. The process as claimed in claim 1, wherein the hydrocarbon feed has a 96%wt. boiling point of at most 560° C.

3. The process as claimed in claim 2, wherein the hydrocarbon feed has a boiling point range of from 30° C. to 350° C.

4. The process as claimed in claim 2, wherein the hydroprocessed synthetic oil fraction comprises at least 50% of said hydrocarbon feed.

5. The process according to claim 2, wherein the thermal cracking is carried out at a temperature of from 700° C. to 1000° C. and at a pressure of from 0.1 bar abs. to 15 bar abs.

6. The process according to claim 1, wherein the thermal cracking is carried out at a residence time of from 0.01 seconds to 1.0 seconds.

7. The process according to claim 4, wherein the hydroprocessed synthetic oil fraction is prepared by hydrogenation of a synthetic oil fraction, at elevated temperature and pressure in the presence of hydrogen and a hydrogenation catalyst.

8. The process as claimed in claim 7, wherein the hydrogenation is carried out at a temperature of from 150° C. to 275° C. and at a pressure of from 20 bar to 120 bar.

9. The process as claimed in claim 8, wherein the hydrogenation is carried out at a weight hourly space velocity of from 0.1 kg/l/h to 5 kg/l/h.

10. The process as claimed in claim 8, wherein the hydrogenation catalyst comprises as catalytically active metal selected from the group consisting of molybdenum, tungsten, cobalt, nickel, ruthenium, iridium, osmium, platinum, palladium, and mixtures thereof.

11. The process according to claim 3, wherein the hydroprocessed synthetic oil fraction is prepared by hydroconversion of a synthetic oil fraction, at elevated temperature and pressure in the presence of hydrogen and a hydroconversion catalyst selected from the group consisting of molybdenum, tungsten, cobalt, nickel, ruthenium, iridium, osmium, platinum, palladium, and mixtures thereof.

12. The process as claimed in claim 11, wherein the hydroconversion is carried out at a temperature of from 250° C. to 375° C. and at a hydrogen partial pressure of from 25 bar to 150 bar.

13. The process as claimed in claim 12, wherein the hydroconversion is carried out at a weight hourly space velocity of from 0.1 kg/l/h to 5 kg/l/h.

14. The process according to claim 12, wherein the hydroprocessed synthetic oil fraction is prepared by hydrocracking of a synthetic oil fraction, at a temperature of from 300° C. to 450° C. and at a pressure of from 25 bar to 200 bar and at a weight hourly space velocity of from 0.1 kg/l/h to 10 kg/l/h and in the presence of hydrogen and a hydrocracking catalyst comprising a Group VIb or VIII metal and faujasite type carrier in the presence of an inorganic oxide binder.

15. A process for preparing lower olefins from a hydrocarbon feed having a 96%wt. boiling point of at most 560° C., and having at least a fraction boiling above the boiling point range of the lower olefins, which process comprises thermal cracking of the hydrocarbon feed, in the presence of an inert diluent consisting of nitrogen or steam, wherein at least 50% of the hydrocarbon feed is a hydroprocessed synthetic oil fraction, prepared by a Fischer-Tropsch synthesis process, which comprises contacting at elevated temperature and pressure a synthesis gas with a catalyst, comprising a metal selected from Group VIII of the Periodic Table and by hydrogenation at a temperature of from 150° C. to 275° C. and at a pressure of from 20 bar to 120 bar.

* * * * *

UNITED STATES PATENT AND TRADEMARK OFFICE
CERTIFICATE OF CORRECTION

PATENT NO. : 5,371,308
DATED : Dec. 6, 1994
INVENTOR(S) : John W. Gosselink; Jocobus Eilers It is certified that error appears in the above-indentified patent and that said Letters Patent is hereby corrected as shown below:

Claim 1, line 10 (column 9, line 52) change "Group VII of the Periodic Table" to --Group VIII of the Periodic Table.--

Signed and Sealed this

Third Day of September, 1996

BRUCE LEHMAN

Attest:

Attesting Officer

Commissioner of Patents and Trademarks